United States Patent [19]
Mehdizadeh

[11] Patent Number: 5,803,904
[45] Date of Patent: Sep. 8, 1998

[54] NERVE ROOT RETRACTOR AND DISC SPACE SEPARATOR

[76] Inventor: Hamid Mehdizadeh, 14928 Diduca Way, Los Gatos, Calif. 95032

[21] Appl. No.: 958,997

[22] Filed: Oct. 28, 1997

[51] Int. Cl.$^6$ .................................................... A61B 17/00
[52] U.S. Cl. ............................................................ 600/235
[58] Field of Search .................................. 600/201, 235, 600/208, 210; 606/238, 96, 53, 86

[56] References Cited

U.S. PATENT DOCUMENTS 3,848,601  11/1974  Ma et al. .
5,123,403   6/1992  Lavyne .................................... 600/235

OTHER PUBLICATIONS

Ray Threaded Fusion Cage, Surgical Technique Manual, ©1996, Surgical Dynamics, 5 pages Incl. pp. 1,2 and 6.

Primary Examiner—Jeffrey A. Smith

[57] ABSTRACT

A nerve retractor and guide for laminectomy procedures has a cylindrical body with a single member extending from one end of the wall of the cylindrical body. The single member is formed to enter the intradiscal space to seat upon and maintain spacing of adjacent vertebral bodies during the procedures. The cylindrical body is positioned adjacent to and protects the cauda equina and the nerve roots that extend therefrom. The wall of the cylinder has a portion cut away on the side thereof opposite the extending single member so that the facet, lamina and pedicle bone areas are visibly accessible for removal as required by the procedures.

11 Claims, 2 Drawing Sheets

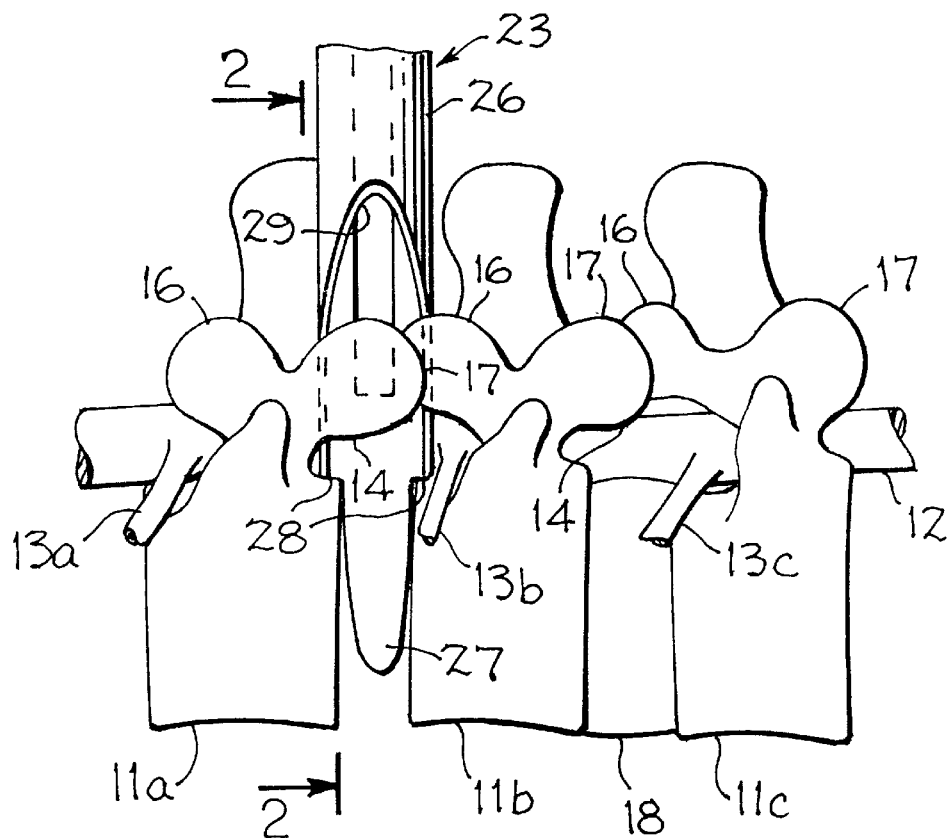
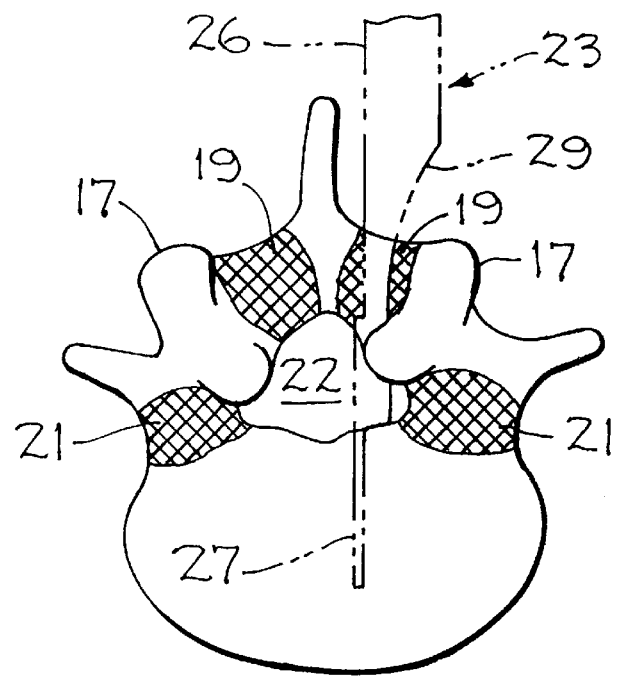

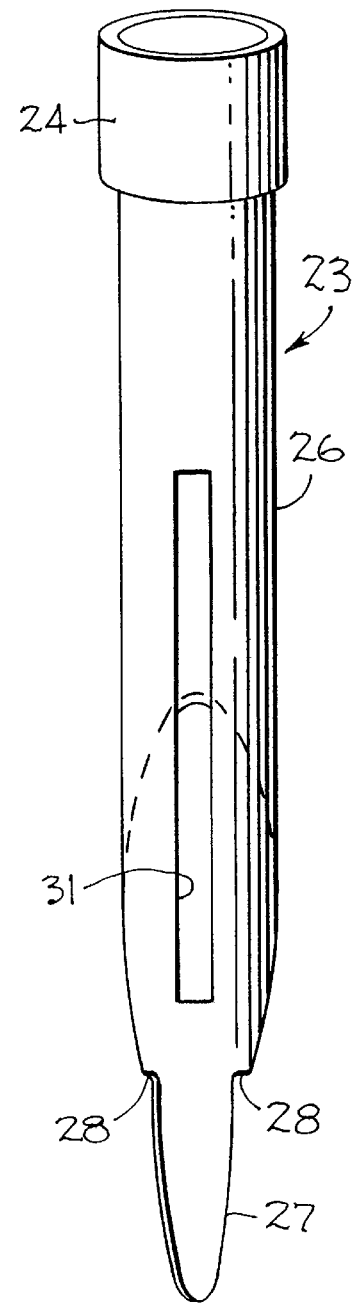
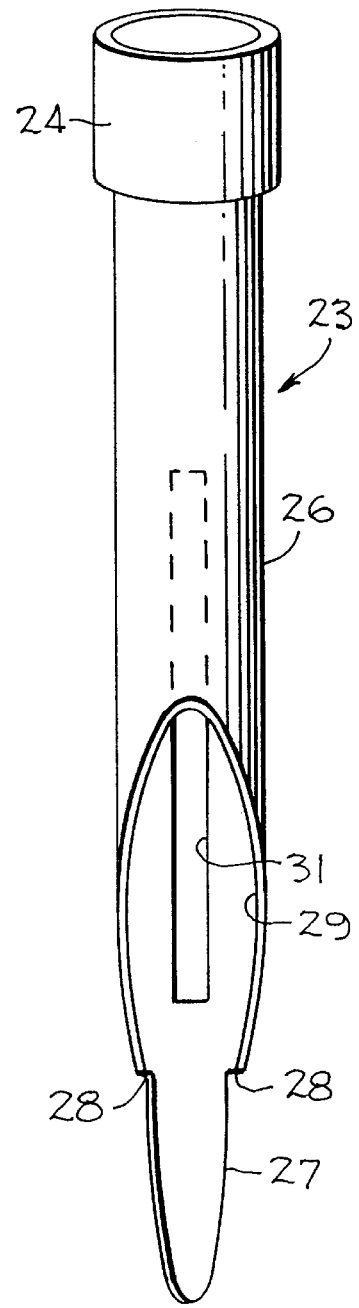
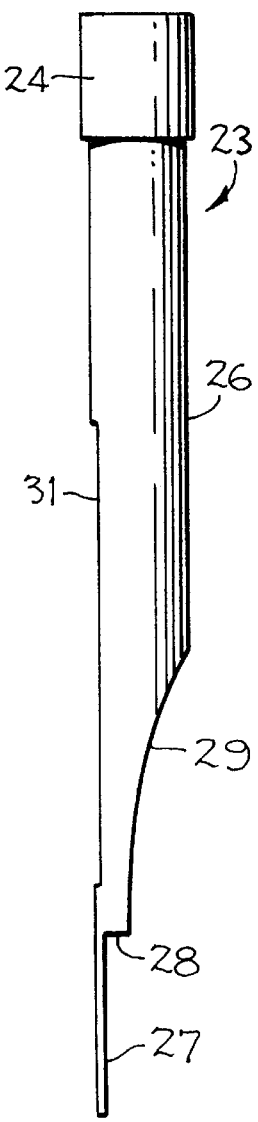

NERVE ROOT RETRACTOR AND DISC SPACE SEPARATOR

SUMMARY OF THE INVENTION

A nerve root retractor and laminectomy guide for protecting the cauda equina and the nerve root and for providing visual access to the lamina, pedicle and facet includes a tubular body having an outside wall, an open interior, a proximal end and a distal end. A tang extends from one side of the outside wall on the distal end. The outside wall has a cut-away portion on an opposite side from the one side from which the tang extends. The cut-away portion extends from the distal end of the tubular body toward the proximal end. In this fashion, insertion of the tang into the intradiscal space from a position adjacent the cauda equina separates adjacent vertebral bodies and protects the nerve root.

In another aspect of the invention a nerve root retractor and disc space spreader is disclosed for contacting vertebral bodies in posterior lumbar surgical procedures. The nerve root retractor includes a tubular body having a body wall, a proximal end and a distal end. A tang extends from one side of the body wall at the distal end. The body wall has a removed portion on an opposing side from the one side from which the tang extends. The removed portion extends from the distal end toward the proximal end. In this fashion, the tang, when seated between vertebral bodies, retracts and protects the nerve root and spreads the vertebral bodies.

A surgical tool is disclosed herein for providing protection to the cauda equina and nerve roots, separation of vertebral bodies and visual access to an operating area during laminectomy procedures. A tubular body has a body wall, a proximal body end and a distal body end. A tang projects from one side of the distal body end and is provided for insertion between the vertebral bodies and for retracting the cauda equina and nerve root. Shoulder means is formed on the distal body end adjacent each side of the extending tang for contacting the edges of adjacent vertebral bodies for limiting penetration into the intradiscal area. The body wall has a cut-away portion in the opposite side thereof from the one side. The cut-away portion extends from the shoulder means toward the proximal body end so that the operating area is visible from within the tubular body through the cut-away portion.

BRIEF DESCRIPTION OF THE DRAWINGS

FIG. 1 shows a series of lumbar vertebrae with the retractor and disc space spreader of the present invention in operating position.

FIG. 2 is a section through the vertebrae in the lumbar region showing the retractor in operating position.

FIG. 3 is an elevation of the nerve root retractor and disc space spreader of the present invention.

FIG. 4 is a perspective of the nerve root retractor and disc space spreader of the present invention.

FIG. 5 is an additional perspective of the nerve root retractor and disc space spreader of the present invention.

DESCRIPTION OF THE PREFERRED EMBODIMENTS

The nerve root retractor and disc space spreader of the present invention is useful in laminectomy procedures. The device of the present invention is useful in many applications including posterior lumbar interbody fusions and fixations (PLIF) procedures. One technique in use at this time is the placement of a threaded fusion cage (Ray TFC, TM) in the space between vertebral bodies in the lumbar region to fuse the adjacent vertebral bodies when a disc which normally occupies the space between the bodies has failed. These fusion cages come in eight sizes, four different diameters and two different lengths, to fit various patient sizes. There are size-specific instrument sets which are used for cage installation as well as universal instrument sets which may be used with any size-specific set of instruments. One of the size-specific instruments is called a tang retractor which has a tubular body, a distal end and a proximal end. Two flat tapered projections extend from the distal end of the retractor that are formed to seat within the intradiscal space between two vertebral bodies. This particular tang retractor is available in four sizes to accommodate the threaded fusion cage diameter which is selected for the specific patient. The known tang retractor with the double extending tangs has a total length of 164 millimeters. The tang lengths are 24 millimeters. The individual widths of the two tangs vary with the size of the retractor. Retractor diameter sizes of 12 millimeters, 14 millimeters, 16 millimeters and 18 millimeters have tang widths of 6 millimeters, 8 millimeters, 10 millimeters and 12 millimeters, respectively. The nerve root retractor and laminectomy guide of the present invention has sizes similar to those of the known double tang retractor.

Certain patient measurements must be made prior to the PLIF procedures to determine the amount of bone which must be removed from a patient to allow the threaded fusion cage (TM) to be put in place. As will be hereinafter described, use of the nerve root retractor of the present invention minimizes bone removal from the pedicle, facet joint and the lamina and also minimizes pressure on the various nerve structure components including the nerve root, ganglion, cauda equina and the dural sac.

Turning to FIG. 1 of the drawings, a series of lumbar vertebrae 11a, 11b and 11c are shown. The cauda equina 12 is also shown passing through the series of vertebrae and having a number of nerve roots 13a, 13b and 13c extending therefrom through spaces termed foramen 14, which spaces are formed in the lateral vertebral structure surrounded by the inferior facet 16, the superior facet 17 and the vertebral bodies 11a, 11b and 11c. A spinal disc 18 is shown situated between the lumbar vertebral bodies 11b and 11c. The inferior and superior facets 16 and 17, respectively, form a joint with connecting cartilage extending therebetween which, together with the shock absorbing discs 18 provide flexibility in the spinal assembly.

With reference now to FIG. 2 of the drawings, the superior facet 17 is shown on each side of a section taken through the spinal structure. A shaded area 19 is also shown on each side of the section of FIG. 2 to represent the lamina bone structure within the vertebrae. Moreover, another pair of shaded areas 21 is shown in the section of FIG. 2 to represent the pedicle bone area within the spinal bone structure. An opening 22 is shown in FIG. 2, through which the cauda equina 12 passes.

With reference now to FIG. 3, the nerve root retractor and disc space spreader 23 of the present invention is shown. An impact portion 24 is shown at the proximal end of the nerve root retractor 23. The retractor has a tubular body 26 with a single tang 27 extending from a distal end of the tubular body 26. Tang or projection 27 is joined to the end of the tubular body 26 at a shoulder 28. Cut-away portion 29 is shown in the tubular body 26 extending from the shoulder 28 toward the proximal end of the nerve root retractor 23.

A clearer arrangement of the configuration of the nerve root retractor is seen in the perspective depictions of FIGS.

4 and 5. The extending tang 27 is seen to be joined by a shoulder 28 on either side thereof to the distal end of the tubular body 26. The cut-away portion 29 in the tubular body 26 is seen to be made in that side of the tubular body which is opposed to the side from which the tang 27 extends. In addition, a window 31 is shown in solid line in FIG. 4 through which a surgeon's assistant may view the operating area within and around the distal end of the tubular body for purposes of applying suction, etc. during the operating procedure. Meanwhile, the surgeon may view the operating area through the cut-away portion 29 of the tubular body 26 which is also in proximity with the operating area. It should be noted that the tang 27 tapers slightly from a larger width at the shoulders 28 to a narrower width at the tip. Otherwise the individual widths of the tangs 27 vary with the size of the root retractor 23 in a fashion similar to the size variations noted hereinbefore for the double tang retractor.

Returning once again to the drawing of FIG. 2, the nerve root retractor 23 is shown in ghost line in position to perform the desired surgical procedure, in this case insertion of the threaded fusion cage (TM) mentioned hereinbefore. It may be seen from the FIG. 2 representation that the insertion of the nerve root retractor 23 requires less bone removal on the side of the retractor which is now occupied by the open cut-away space 29 than would be the case if a tang occupied the cut-away space, because it is only necessary to remove bone to accept the threaded fusion cage and no extra bone is required to be removed to accept an additional tang.

The nerve root retractor 23 is shown in solid lines in FIG. 1 in a position corresponding to the position shown in FIG. 2 in ghost line. The retractor may be seen to be seated firmly against adjacent vertebral bodies 11a and 11b on the shoulders 28 on opposing sides of the extending tang 27. The cut-away portion 29 in the tubular body 26 is shown in FIG. 1 to provide visual access to the operating area for bone removal from the facet 17, lamina area 19 and pedicle area 21 as necessary to prepare for the threaded fusion cage (TM) placement, or for placement of other materials as required by the specific operating procedures. The tang 27 is placed within the intradiscal space to its full length by tapping the impact cap 24 with a mallet (not shown) until the shoulders 28 rest on adjacent vertebral bodies 11a and 11b as shown in FIG. 1. It should be noted that bone removal may be undertaken for decompression of a nerve root by removing parts of the lamina or the inferior and superior facets visually, because visual access is provided to the bone areas of interest by the cut-away portion 29. With only one tang on the end of the tubular body 26 the retraction required of the nerve root and the cauda equinais not as severe. The nerve root and cauda equina are not stressed as much because of the diminished retractor structure created by the opening 29, and further they are offered protection by the single tang 27 of the retractor 23. The lessening of bone removal provides greater anatomical strength in the finished procedure. In addition, the configuration of the nerve retractor of the present invention provides convenience to the operating surgeon due to the visual access provided by the nerve root retractor of the present invention. While the nerve root retractor has been described herein in conjunction with positioning the threaded fusion cage (TM), it may be used in the performance of any laminectomy or PLIF procedure and for the deposition of any materials used in carrying out those procedures.

Although the best mode contemplated for carrying out the present invention has been shown and described herein, it will be understood that modification and variation may be made without departing from what is regarded to be the subject matter of the invention.

What is claimed:

1. A nerve root retractor and laminectomy guide for protecting the cauda equina and the nerve root and providing visual access to the lamina, pedicle and facet, comprising a tubular body having an outside wall, an open interior, a proximal end and a distal end, and a tang extending from one side of said outside wall on said distal end, said outside wall having a cut away portion on an opposite side from said one side, said cut away portion extending from said distal end toward said proximal end, whereby insertion of said tang into the intradiscal space from a position adjacent the cauda equina separates adjacent vertebral bodies and protects the nerve root.

2. The nerve root retractor of claim 1 wherein said tubular body has a window opening in said outside wall on said one side extending from a position spaced from said distal end toward said proximal end, whereby regions adjacent to said distal end are observable during the laminectomy.

3. The nerve root retractor of claim 1 comprising an impact cap for positioning on said proximal end.

4. The nerve root retractor of claim 1 comprising a shoulder on each side of said tang at said distal end extending between said tang and said cut away portion.

5. A nerve root retractor and disc space spreader for contacting vertebral bodies in posterior lumbar surgical procedures, comprising a tubular body having a body wall, a proximal end and a distal end, and a tang extending from one side of said body wall at said distal end, said body wall having a removed portion on an opposing side from said one side, said removed portion extending from said distal end toward said proximal end, whereby said tang when seated between vertebral bodies retracts and protects the nerve root and spreads the vertebral bodies.

6. The nerve root retractor of claim 5, said body wall having a window opening therein on said one side extending from a position spaced from said distal end toward said proximal end.

7. The nerve root retractor of claim 5 comprising an impact cap for positioning on said proximal end.

8. The nerve root retractor of claim 5 comprising a shoulder on each side of said tang at said distal end extending between said tang and said cut away portion for locating said tang relative to adjacent vertebral bodies.

9. A surgical tool for providing protection to the cauda equina and nerve roots, separation of vertebral bodies and visual access to an operating area during laminectomy procedures, comprising a tubular body having a body wall, a proximal body end and a distal body end, a tang projecting from one side of said distal body end for insertion between the vertebral bodies and for retracting the cauda equina and nerve root, and shoulder means on said distal body end adjacent each side of said tang for contacting the edges of adjacent vertebral bodies for limiting penetration into the intradiscal area, said body wall having a cut away portion in the opposite side thereof from said one side, said cut away portion extending from said shoulder means toward said proximal body end, whereby the operating area is visible through said cut away portion.

10. The surgical tool of claim 9 wherein said tubular body has a window opening in said body wall on said one side extending from a position spaced from said distal body end toward said proximal body end.

11. The surgical tool of claim 9 comprising an impact cap on said proximal body end.

\* \* \* \* \*